United States Patent
Messick

(12) United States Patent (10) Patent No.: US 6,315,557 B1
(45) Date of Patent: Nov. 13, 2001

(54) ROTARY DENTAL INSTRUMENT AND METHODS OF USE

(75) Inventor: Keith Messick, Garden Grove, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/533,346

(22) Filed: Mar. 23, 2000

(51) Int. Cl.⁷ .................................................. A61C 1/10
(52) U.S. Cl. ............................ 433/84; 433/82; 433/99
(58) Field of Search ................................ 433/80, 82, 84, 433/98, 99, 100

(56) References Cited

U.S. PATENT DOCUMENTS

| | | | | |
|---|---|---|---|---|
| 4,117,861 | * | 10/1978 | Betush | 137/595 |
| 4,276,023 | * | 6/1981 | Phillips et al. | 433/85 |
| 4,276,024 | * | 6/1981 | Warrin | 433/99 |
| 5,338,194 | * | 8/1994 | Strohmaier | 433/82 |
| 5,538,423 | * | 7/1996 | Coss et al. | 433/27 |
| 5,934,904 | * | 8/1999 | Elrod et al. | 433/88 |

* cited by examiner

*Primary Examiner*—Ralph A. Lewis
(74) *Attorney, Agent, or Firm*—Wood, Herron & Evans, LLP

(57) ABSTRACT

A rotary dental instrument for rotating a cutting tool at a repair site of a patient's tooth and providing an irrigating liquid to the repair site. The instrument includes a handpiece having a rotating file coupled to a motor and an irrigating port coupled to a pump. A control associated with the instrument automatically starts discharge of the irrigating liquid from the port at a predetermined time after starting the motor. This provides an automatic delay between rotation of the rotatable element holding the file and discharge of irrigating liquid from the port. A corresponding method involves providing a starting input to the motor, waiting a predetermined amount of time after the cutting tool or rotatable element begins rotating, and automatically discharging the irrigating liquid after the predetermined amount of time has elasped.

7 Claims, 2 Drawing Sheets

ROTARY DENTAL INSTRUMENT AND METHODS OF USE

FIELD OF THE INVENTION

The present invention generally relates rotary dental cutting instruments and, more specifically, to rotary cutting instruments having irrigating features and to the controls used for the rotating cutting tool and the supply of irrigating liquid to the repair site on a tooth.

BACKGROUND OF THE INVENTION

Many current and past motorized handpieces have been used by dental professionals to rotate a file or other cutting instrument and to simultaneously supply an irrigating liquid, such as in the form of a water jet, to rinse the repair site during the cutting operation. These instruments are especially useful during root canal procedures. The water jet commences upon activation of the handpiece motor and, therefore, commences simultaneously with rotation of the cutting tool.

Unfortunately, the simultaneous activation of the motor and initiation of the irrigating liquid causes the liquid to strike the rotating cutting tool before the tip of the cutting tool can be located at the repair site, such as within the root canal of a tooth. The resulting spray makes it difficult to see the repair site, such as the root canal opening, and this, in turn, makes insertion of the rotating cutting tool into the root canal potentially more error prone. Also, the user typically clamps the file within the jaws of the instrument by briefly activating the motor with the tip located outside the patient's mouth. This leads to an undesirable spray of liquid outside the patient's mouth as well.

For the foregoing reasons, and to solve various problems in this area, it would be desirable to provide a rotary dental instrument and methods which allow the dental professional to present the cutting tool at the repair site prior to an automatic initiation of the irrigating liquid.

SUMMARY OF THE INVENTION

The present invention provides a rotary dental instrument for rotating a cutting tool at a repair site, such as in a root canal of a patient's tooth, and providing an irrigating liquid to the repair site in an automatic, but delayed manner following activation of the cutting tool. Preferably, the delay provides a sufficient time period to allow the cutting tool to be precisely positioned at or within the repair site before commencement of the irrigating liquid discharge. The delay can also allow the user to briefly activate the motor, without simultaneous liquid discharge to tighten the jaws around the cutting tool at the instrument tip.

More specifically, the instrument comprises a handpiece having a rotating element for receiving and rotating a cutting tool and at least one irrigating port for discharging the irrigating liquid generally at the repair site. A motor is electrically coupled to the rotating element for rotating the cutting tool. A pressurized irrigating liquid supply is fluidly coupled to the irrigating port and supplies the irrigating liquid through the irrigating port in a pressurized manner. In the preferred embodiments, the pressurized irrigating liquid supply includes a pump having a liquid output coupled in fluid communication with the irrigating port. A control is operatively coupled with the motor and the pressurized irrigating liquid supply. The control automatically starts discharge of the irrigating liquid from the irrigating port at a predetermined time after starting operation of the motor. This provides an automatic delay between rotation of the rotating element and discharge of the irrigating liquid from the irrigating port. The predetermined time which provides for the delay may be chosen as a time period allowing the dental professional using the instrument to rotate the cutting tool or the rotatable element holding the cutting tool for any desired purpose prior to initiation of the liquid discharge.

Two alternative manners of providing for the delay are currently preferred. In one embodiment, the control receives an input from a user and, in response to the input, the control sends respective signals to initiate the operation of the motor and the pump. The signal sent to initiate operation of the pump is delayed with respect to the signal sent to initiate operation of the motor. As one of several different possible examples, this delay may be provided by an electronic timer, such as a one-shot timer, which receives a signal from a controller and, after a predetermined time, such as about one second, sends the signal to a device, such as a relay, which closes to start the pump. In another embodiment, a power delay device may be used to delay transmission of electrical power to the pump until a predetermined time after initiation of the motor driving the cutting tool. This power delay device may include a timer coupled with a power relay, for example, in which the timer receives the signal from the controller upon activation of the motor driving the cutting tool and, after the predetermined time, activates the power relay to close the power circuit which includes the pump. In this embodiment, the signal from the controller is not delayed but rather the high voltage power itself is delayed by the power delay device. It will be appreciated that many other control schemes may be used to provide for the automatic delay contemplated by the present invention and that the two embodiments detailed herein, i.e., the signal delay and the power delay, may be modified or substituted in many ways while still falling within the inventive concepts.

The invention further contemplates a method of performing a cutting operation on the tooth of a patient with an instrument as generally discussed above. The method includes providing a starting input to the electrically operated rotary instrument to thereby rotate an element thereof holding a cutting tool, waiting a predetermined amount of time after the rotating element begins rotating, and automatically discharging the irrigating liquid proximate the cutting tool after the predetermined amount of time has elapsed.

Additional features, objectives and advantages of the invention will become more readily apparent to those of ordinary skill in the art upon review the following detailed description of the preferred embodiments, taken in conjunction with the drawings.

DETAILED DESCRIPTION OF THE PREFERRED EMBODIMENTS

Figure 1:
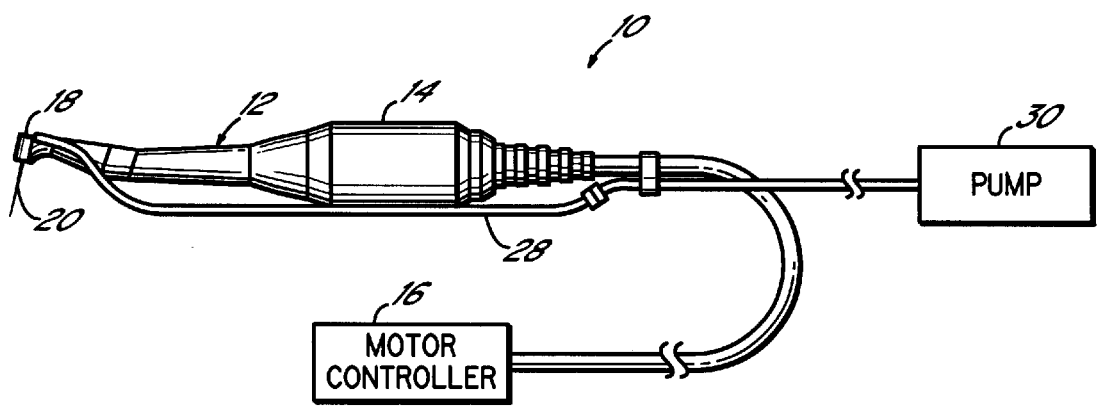
FIG. 1 is a schematic illustration showing a rotary dental instrument constructed in accordance with the invention.
Figure 1A:
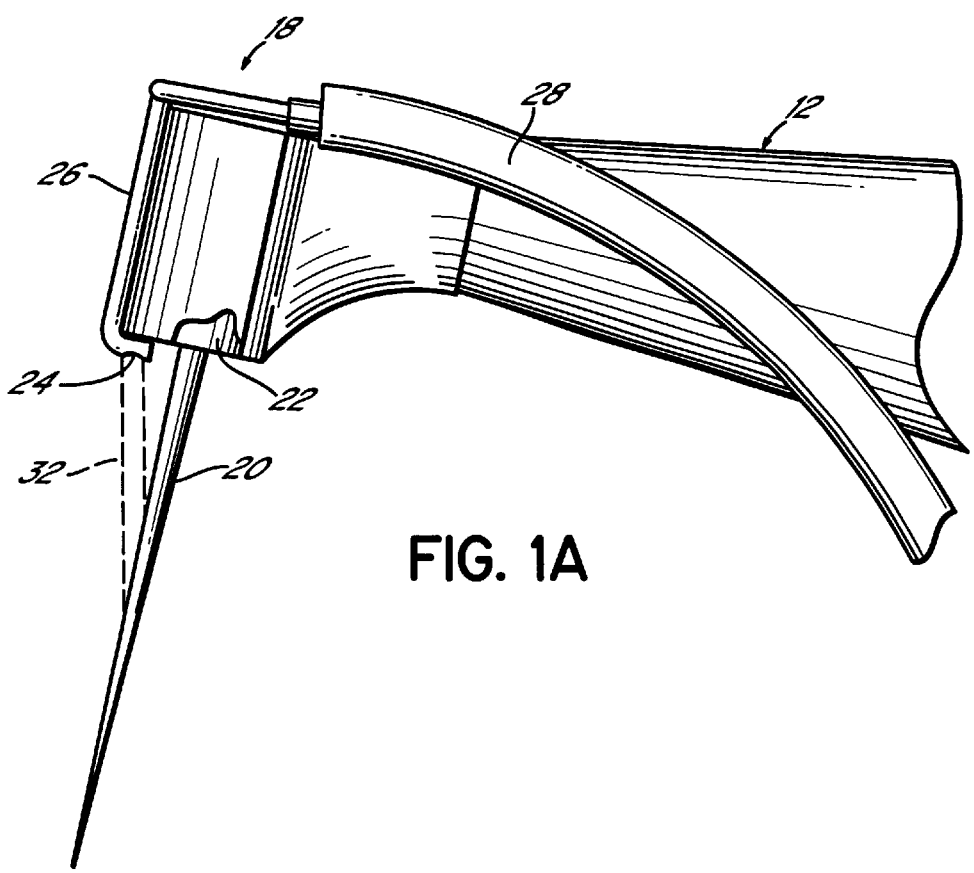
FIG. 1A is an enlarged view of the cutting and irrigating tip of the instrument shown in FIG. 1.

Referring first to FIGS. 1 and 1A, a rotary instrument 10 constructed in accordance with the invention preferably includes a handpiece 12 coupled with a motor 14. Handpiece 12 may be physically connected to motor 14 and its housing or, optionally, may be separated from motor 14 to allow easier handling of handpiece 12 during use. Motor 14 is coupled with a motor controller 16, as will be discussed below. Handpiece 12 includes a tip 18 having a file 20 coupled to motor 14 to facilitate rotation during use. File 20 may be substituted with other cutting tools depending on the application. File 20 is especially useful during root canal procedures. As shown in FIG. 1A, a rotatable element 22, which typically comprises jaws which may be tightened and loosened to allow retention and removal of file 20, is coupled for rotation by motor 14. Various drive elements may be used between rotatable element 22 and motor 14, including conventional gearing and/or flexible drive shafts. Tip 18 further includes an irrigating port 24 at the end of a conduit 26 which is fluidly coupled with a flexible tube 28. Tube 28 is connected to the output of a pump 30 which supplies the irrigating liquid, such as water.

Figure 2:
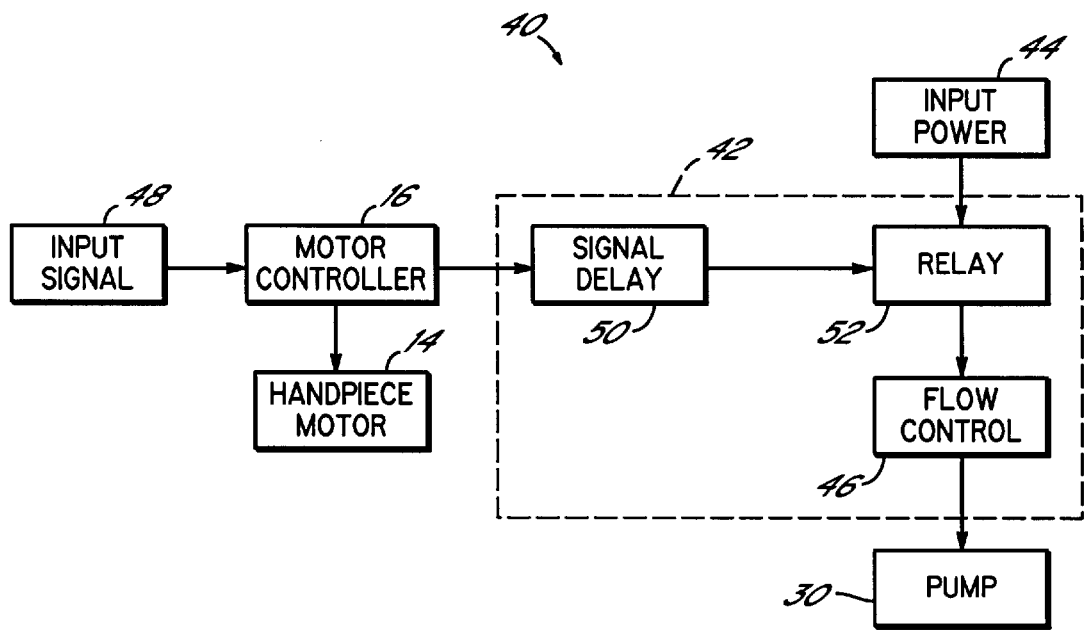
FIG. 2 is a schematic illustration of one control system used to operate the instrument of FIG. 1.

Turning to FIG. 2, a first embodiment of a control system 40 for instrument 10 includes motor controller 16 which is electrically coupled with a control 42 for operating pump 30. Pump 30 receives electrical operating power from input power source 44 and may include a conventional flow control 46 such that the dental professional can regulate and change the flow of water through pump 30. Control 42 determines the timing of the operation of pump 30 relative to the operation of handpiece motor 14. Specifically, when the user provides an input signal 48, such as by depressing a button (not shown) on handpiece 12 (FIG. 1), motor controller 16 will simultaneously send signals to handpiece motor 14 to initiate rotation of cutting tool or file 20 and simultaneously provide a signal to signal delay device 50. Signal delay device 50 may comprise, as one example, a one-shot timer that provides an output signal at a predetermined time after receipt of the signal from motor controller 16. After the predetermined time delay, which is preferably at least 0.5 (½) second and, most preferably, between about one to two seconds, signal delay device 50 transmits the output signal to a relay 52 which closes in response to the output signal to complete the power circuit to pump 30. Upon closing of relay 52, power is provided by input power source 44 to operate pump 30 and initiate the supply of irrigating liquid 32 as shown in FIG. 1A. The automatic delay provided by control 42, and more particularly signal delay 50, allows the dental professional to present rotating file 20 to the repair site, such as by inserting rotating file 20 within a patient's root canal, prior to irrigating liquid 32 being discharged from irrigation port 24. In this way, the rotating file 20 may be properly positioned in the root canal without irrigating liquid 32 spraying or otherwise obstructing the user's view. During changeover of files 20, the delay also provides enough time for the user to initiate the motor briefly to clamp file 20 within rotatable element 22 without discharging liquid 32. While signal delay 50 has been described as a one-shot timer, those skilled in the art will recognize that other components, used either alone or in combination, can facilitate a similar result.

Figure 3:
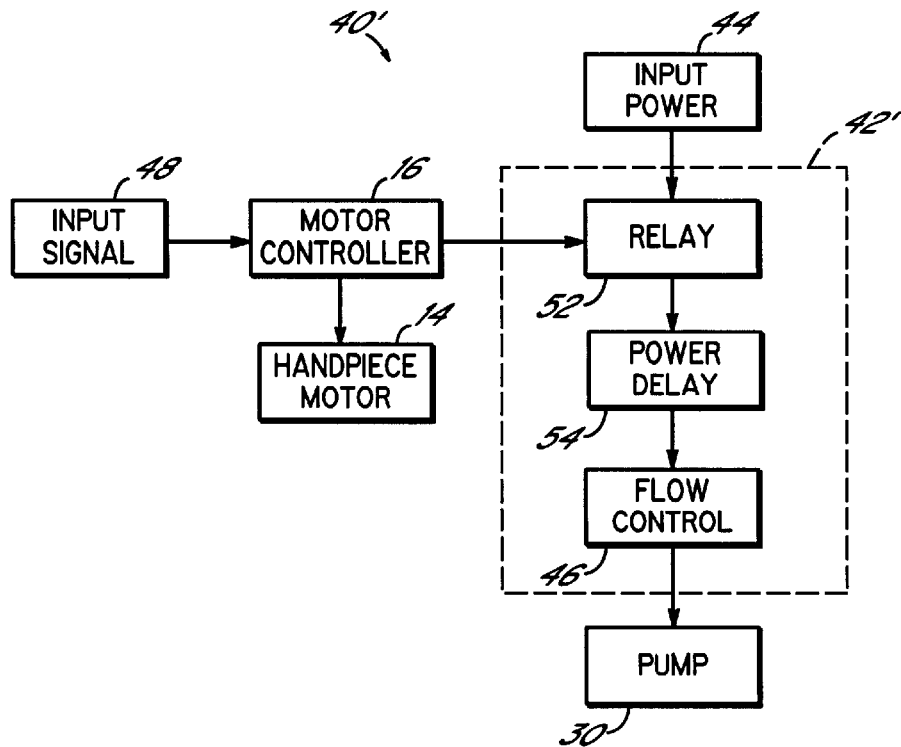
FIG. 3 is another embodiment of a control system used to operate the instrument of FIG. 1.

Referring now to FIG. 3, in which like numerals represent like elements between the embodiments and in which reference numerals having prime (') marks indicate modified elements, a control system 40' provides a different manner of delaying the relative activation of motor 14 and pump 30. In this embodiment, a power delay device 54 is coupled between relay 52 and pump 30. When the user provides input signal 48 to motor controller 16, motor controller again provides signals to handpiece motor 14 and control 42'. Relay 52 is closed or activated to allow for the transmission of power from input power source 44, however, power delay device 54 delays the transmission of power to speed control 46 and pump 30 for a predetermined time period which, again, may be about one second. Thus, in this embodiment, the signal from motor controller 16, which is a low voltage signal, is not delayed prior to closing relay 52, but rather, the high voltage power itself from power source 44 through relay 52 is delayed by power delay device 54 upon receipt by control 42' of the signal from motor controller 16. Power delay device 54 may, for example, comprise a power relay and a timer in which the timer activates or closes the relay after a predetermined time period to close the power circuit and provide electrical operating power to activate pump 30.

It will be appreciated that control systems 40 and 42' represent only two of many possible control systems for providing the automatic delay between discharge of irrigating liquid 32 and rotation of file 20. Other electrical and/or mechanical components may be utilized to provide the same feature. For example, a solenoid valve may be used to control the discharge of irrigating liquid in a delayed fashion instead of directly delaying the activation of pump 30.

While the present invention has been illustrated by a description of these preferred embodiments and while these embodiments have been described in some detail, it is not the intention of the Applicant to restrict or in any way limit the scope of the appended claims to such detail. Additional advantages and modifications will readily appear to those skilled in the art. This has been a description of the present invention, along with the preferred methods of practicing the present invention as currently known. Various aspects of this invention may be used alone or in different combinations.

The scope of the invention itself should only be defined by the appended claims, wherein I claim:

1. A rotary dental instrument for rotating a cutting tool at a repair site of a patient's tooth and providing an irrigating liquid to the repair site, the instrument comprising:

a handpiece having a motor-driven rotating element for receiving and rotating the cutting tool when the rotating element is driven and at least one irrigating port for discharging the irrigating liquid generally at the repair site, a motor coupled to said rotating element for rotating the cutting tool, a pressurized irrigating liquid supply fluidly coupled to the irrigating port and operative to supply the irrigating liquid through said irrigating port in a pressurized manner, and a control operatively coupled with said motor and said pressurized irrigating liquid supply, said control operative to automatically delay the start of discharge of said irrigating liquid from said irrigating port for a predetermined time with respect to the start of rotation of said motor-driven rotating element, wherein said control receives an input from a user and, in response to the input, sends respective signals to initiate rotation of said motor-driven rotating element and said pressurized irrigating liquid supply, the signal sent to initiate operation of said pressurized irrigating liquid supply being delayed with respect to the signal sent to initiate rotation of said motor-driven rotating element, thereby providing an automatic delay between rotation of said rotating element and discharge of said irrigating liquid from said irrigating port.

2. The rotary dental instrument of claim 1, wherein said pressurized irrigating liquid supply includes a pump having a liquid output coupled in fluid communication with said irrigating port.

3. The rotary dental instrument of claim 2, wherein said control further comprises a signal delay device including a timer for delaying the signal sent to initiate operation of the pump.

4. A rotary dental instrument for rotating a cutting tool at a repair site in a patient's tooth and providing an irrigating liquid to the repair site, the instrument comprising:

- a handpiece having a rotating element for receiving and rotating the cutting tool and at least one irrigating port for discharging the irrigating liquid generally at the repair site,
- a motor coupled to said rotating element for rotating the cutting tool,
- an electrically operated pump having a liquid discharge output fluidly coupled to the irrigating port and operative to pump the irrigating liquid through said port, and
- a motor controller electrically coupled with said motor and said pump, said motor controller having a first output operative to start operation of said motor upon receiving an input signal initiated by a user, said motor controller further having a second output operative to initiate operation of said pump, and
- a timing device coupled between the second output and the pump and responsive to the second output for delaying the operation of said pump until a predetermined time after initiation of the motor operation.

5. A rotary dental instrument for rotating a cutting tool at a repair site of a patient's tooth and providing an irrigating liquid to the repair site, the instrument comprising:

- a handpiece having a motor-driven rotating element for receiving and rotating the cutting tool when the rotating element is driven and at least one irrigating port for discharging the irrigating liquid generally at the repair site,
- a motor coupled to said rotating element for rotating the cutting tool,
- a pressurized irrigating liquid supply fluidly coupled to the irrigating port and operative to supply the irrigating liquid through said irrigating port in a pressurized manner, and
- a control operatively coupled with said motor and said pressurized irrigating liquid supply, said control operative to automatically delay the start of discharge of said irrigating liquid from said irrigating port for a predetermined time with respect to the start of rotation of said motor-driven rotating element, wherein said control receives an input from a user and, in response to the input, sends respective signals to initiate rotation of said motor-driven rotating element and said pressurized irrigating liquid supply, further comprising a power delay device coupled to said control and said pressurized irrigating liquid supply, said power delay device receiving without delay the signal sent to initiate operation of said pressurized irrigating liquid supply and operating to delay transmission of electrical power to said pressurized irrigating liquid supply for said predetermined time, thereby providing an automatic delay between rotation of said rotating element and discharge of said irrigating liquid from said irrigating port.

6. The rotary dental instrument of claim 5, wherein said power delay device includes a timer.

7. The rotary dental instrument of claim 5, wherein said pressurized irrigating liquid supply includes a pump having a liquid output coupled in fluid communication with said irrigating port.

* * * * *